United States Patent [19]
Muller

[11] Patent Number: 5,324,281
[45] Date of Patent: Jun. 28, 1994

[54] LASER REPROFILING SYSTEM EMPLOYING A PHOTODECOMPOSABLE MASK

[75] Inventor: David F. Muller, Boston, Mass.

[73] Assignee: Summit Technology, Inc., Waltham, Mass.

[21] Appl. No.: 964,925

[22] Filed: Oct. 22, 1992

Related U.S. Application Data

[63] Continuation of Ser. No. 591,616, Oct. 2, 1990, abandoned, which is a continuation-in-part of Ser. No. 124,101, Jan. 15, 1988, Pat. No. 4,994,058, which is a continuation-in-part of Ser. No. 19,200, Mar. 9, 1987, Pat. No. 4,856,573, and a continuation-in-part of Ser. No. 392,782, Aug. 11, 1989, Pat. No. 5,019,074.

[51] Int. Cl.$^5$ .............................................. A61B 5/06
[52] U.S. Cl. ........................................ 606/5; 606/3; 606/17; 219/121.6; 219/121.73; 219/121.85
[58] Field of Search .................. 128/375, 898; 606/2, 606/3, 5, 10–19; 219/121.6, 121.68–121.69, 121.73–121.77, 121.83, 121.85; 359/297

[56] References Cited

U.S. PATENT DOCUMENTS

| | | | |
|---|---|---|---|
| 3,558,208 | 1/1971 | Hudson | 350/314 |
| 3,703,176 | 11/1972 | Vassilliadis et al. | 128/394 |
| 3,769,963 | 11/1973 | Goldman et al. | 128/2 R |

(List continued on next page.)

FOREIGN PATENT DOCUMENTS

| | | |
|---|---|---|
| EP0280414 | of 0000 | European Pat. Off. . |
| EP0346116 | of 0000 | European Pat. Off. . |
| 111060 | 6/1984 | European Pat. Off. . |
| 151869 | 8/1985 | European Pat. Off. . |
| 152686 | 8/1985 | European Pat. Off. . |
| 207648 | 1/1987 | European Pat. Off. . |
| 224322 | 6/1987 | European Pat. Off. . |
| 274205 | 7/1988 | European Pat. Off. . |
| 3148748 | 7/1983 | Fed. Rep. of Germany . |
| 3535072 | 4/1987 | Fed. Rep. of Germany . |
| 3535073 | 4/1987 | Fed. Rep. of Germany . |
| 2626465 | of 0000 | France . |
| WO87/05496 | 9/0987 | PCT Int'l Appl. . |
| WO86/04500 | 8/1986 | World Int. Prop. O. . |
| 8705496 | 9/1987 | World Int. Prop. O. ............ 606/5 |

OTHER PUBLICATIONS

Fine et al., "Preliminary Observations On Ocular Effects ...", vol. 64, No. 2, *American Journal of Ophthalmology*, pp. 209–222 (Aug. 1967).

Beckman, et al., "Limbectomies, Keratectomies, and Keratostomies Performed..." vol. 71, *American Journal of Ophthalmology*, pp. 1277–1283 (Jun. 1971).

Mainster, "Ophthalmic Applications of Infrared Lasers–Thermal Considerations" vol. 18, No. 4, *Invst. Ophthal. and Vis. Sci.*, pp. 414–420 (1979).

Peyman, et al., "Modification of Rabbit Corneal Curvature with Use of Carbon Dioxide Laser Burns", vol. 11, No. 5, *Ophthalmic Surgery*, pp. 325–329 (May 1980).

Keates et al., "Carbon Dioxide Laser Beam Control for Corneal Surgery", vol. 12, No. 2, *Ophthalmic Surgery*, pp. 117–122, (Feb. 1981).

(List continued on next page.)

*Primary Examiner*—David M. Shay
*Attorney, Agent, or Firm*—Thomas J. Engellenner

[57] ABSTRACT

A laser system for reprofiling a surface, such as the corneal surface of an eye, comprising a laser and a photoreactive mask disposed between the laser means and the surface for providing a predefined profile of resistance to laser radiation, such that, upon irradiation of the mask, a portion of the laser radiation is selectively absorbed and another portion is transmitted to the surface, in accordance with the mask profile, to selectively erode the surface. The mask can be connected to the support structure and disposed in optical alignment with the laser means and the surface. The mask can be directly integrated with support structure attached to the surface or spatially separated from the surface and imaged onto the surface. In one preferred embodiment, the mask includes a transparent matrix and light-absorbing dispersoids selectively distributed within the matrix, such that the dispersed elements are progressively bleached by exposure to the laser radiation.

11 Claims, 3 Drawing Sheets

U.S. PATENT DOCUMENTS

| | | | |
|---|---|---|---|
| 3,941,973 | 3/1976 | Luck, Jr. et al. | 219/121 |
| 3,982,541 | 9/1976 | L'Esperance, Jr. | 128/303.1 |
| 4,173,980 | 11/1979 | Curtin | 128/303 R |
| 4,266,549 | 5/1981 | Kimura | 128/303.1 |
| 4,309,998 | 1/1982 | Aaron nee Rosa et al. | 128/303.1 |
| 4,326,529 | 4/1982 | Doss et al. | 128/303.1 |
| 4,378,567 | 3/1983 | Mir | 358/75 |
| 4,381,007 | 4/1983 | Doss | 128/303.1 |
| 4,461,294 | 7/1984 | Baron | 128/303.1 |
| 4,527,043 | 7/1985 | Hashiura et al. | 219/121 |
| 4,538,608 | 9/1985 | L'Esperance, Jr. | 128/303.1 |
| 4,648,400 | 3/1987 | Schneider et al. | 128/303.1 |
| 4,665,913 | 5/1987 | L'Esperance, Jr. | 128/303.1 |
| 4,669,466 | 6/1987 | L'Esperance | 128/303.1 |
| 4,686,979 | 8/1987 | Gruen et al. | 128/303.1 |
| 4,718,418 | 3/1988 | L'Esperance, Jr. | 128/303.1 |
| 4,721,379 | 1/1988 | L'Esperance | 351/212 |
| 4,729,372 | 3/1988 | L'Esperance, Jr. | 128/303.1 |
| 4,732,148 | 3/1988 | L'Esperance, Jr. | 128/303.1 |
| 4,770,172 | 9/1988 | L'Esperance, Jr. | 128/303.1 |
| 4,773,414 | 9/1988 | L'Esperance, Jr. | 128/303.1 |
| 4,798,204 | 1/1989 | L'Esperance, Jr. | 128/303.1 |
| 4,838,266 | 6/1989 | Koziol et al. | 606/5 |
| 4,856,513 | 8/1989 | Muller | 606/5 |
| 4,911,711 | 3/1990 | Telfair et al. | 606/5 |
| 4,994,058 | 2/1991 | Raven et al. | 606/5 |
| 5,019,074 | 5/1991 | Muller | 606/5 |

OTHER PUBLICATIONS

Girard, "Refractive Keratoplasty", vol. 2, *Corneal Surgery*, pp. 142–171 (1981).

Taboada et al., "Reponse of the Corneal Epithelium to KrF Excimer Laser Pulses", vol. 40, *Health Physics*, pp. 677–683 (May 1981).

Chetverukhin et al., "Refraction Thermokeratoplasty and Laser Keratoplasty", *Vestn. Oftal.*, pp. 67–69 (U.S.S.R 1982).

Srinivasan et al., "Far-UV Photoetching of Organic Material", *Laser Focus*, (May 1983).

Srinivasan, "Kinetics of the Ablative Photodecomposition of Organic Polymers . . . ", vol. B1, *J. of Vac. Sci. Technol.*, pp. 923–926 (1983).

Srinivasan, "Action of Far-Ultraviolet Light on Organic Polymer Films . . . ", pp. 12–14 (Oct. 1983).

Trokel, et al. "Excimer Laser Surgery of the Cornea", vol. 96, *American Journal of Ophthalmology*, pp. 710–715 (1983).

Galbavy, "Use of Diamond Knives in Ocular Surgery", vol. 15, No. 3, *Ophthalmic Surgery*, pp. 203–205 (Mar. 1984).

Puliafito et al., "Excimer Laser Ablation of the Cornea and Lens", vol. 92, No. 6, *Ophthalmology*, pp. 741–748 (Jun. 1985).

L'Esperance, Jr., "Current Status of Ophthalmic Photovaporization Therapy", *Trans. New Orleans Acad. of Ophthalmol*, pp. 231–255 (1985).

O'Hara et al., vol. 11 *IBM Technical Disclosure Bulletin*, pp. 1168–1169 (1969).

Binder et al., "Refractive Keratoplasty", vol. 100, *Arch. Ophthalmol.* pp. 802–806 (1982).

L'Esperance, New Laser Systems and Their Potential Clinical Usefulness, 1985, *Transactions of the New Orleans Academy of Ophthalmology*.

Muller et al., "Studies of Organic Molecules as Saturable Absorbers at 193 nm," IEEE Journal of Quantum Electronics, vol. QE-18, No. 11.

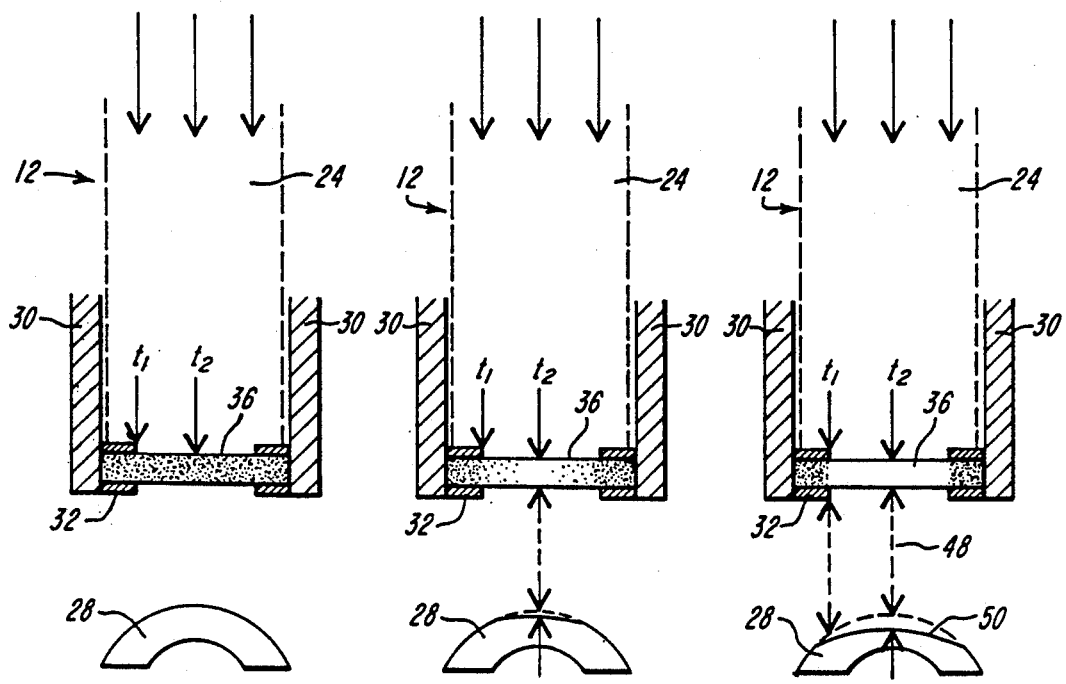
FIG. 4A  FIG. 4B  FIG. 4C
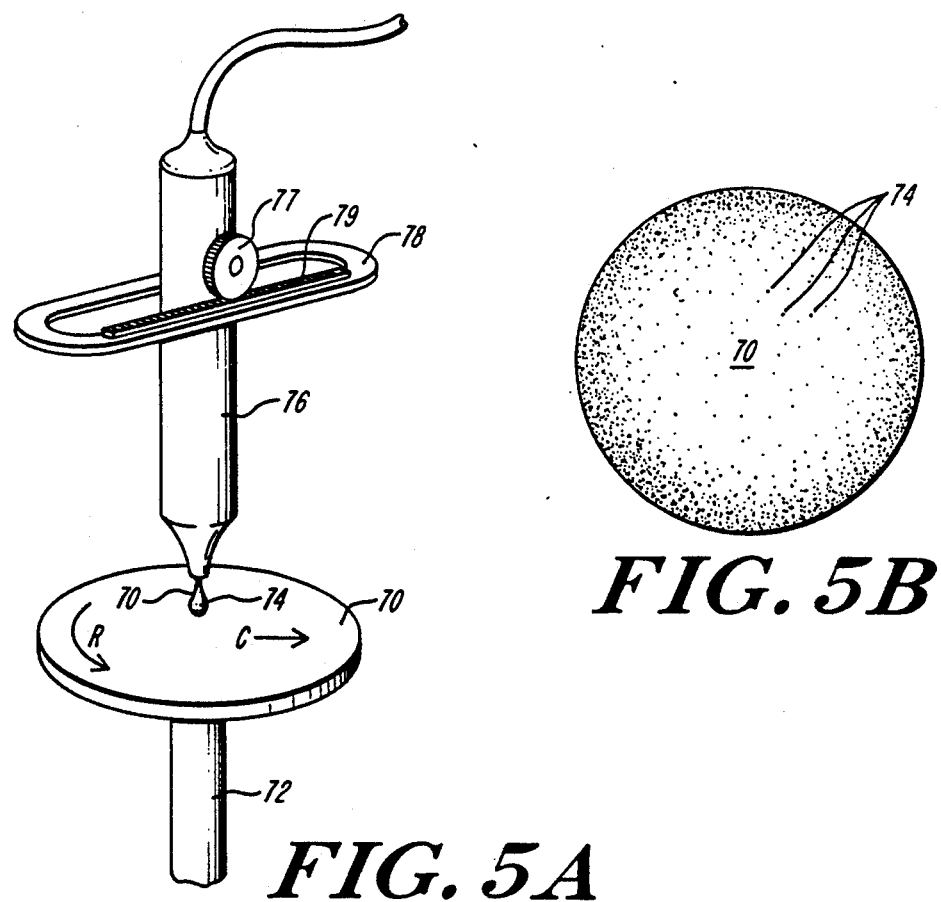
FIG. 5B
FIG. 5A

LASER REPROFILING SYSTEM EMPLOYING A PHOTODECOMPOSABLE MASK

REFERENCE TO RELATED APPLICATIONS

This application is a continuation of application Ser. No. 591,616, now abandoned, filed Oct. 2, 1992, which is a continuation-in-part of application Ser. No. 124,101 filed on Jan. 15, 1988, now U.S. Pat. No. 4,994,058, which was a continuation-in-part of application Ser. No. 019,200 filed Mar. 9, 1987, now U.S. Pat. No. 4,856,513, and also a continuation-in-part of application Ser. No. 392,782 filed Aug. 11, 1989, now U.S. Pat. No. 5,019,074.

BACKGROUND OF THE INVENTION

The technical field of this invention is laser ablation of surfaces, especially surfaces of biological materials. In particular, the invention relates to systems and methods for reprofiling the cornea of the eye.

It is known to employ laser sources to erode surfaces of workpieces and the like. Such apparatus is in general relatively complex and demands highly skilled use. It is an object of the present invention to provide improved and simplified apparatus and method for eroding surfaces.

It is also an object of the present invention to provide an improvement whereby laser techniques can be applied to sensitive surfaces and, in particular, to objects in which it would be undesirable to affect underlying layers.

In the field of medicine, a known technique for the treatment of certain forms of myopia is surgically to remove a segment of the collagen sub-surface layer of the eye, to reshape the removed segment as by surgical grinding, and to restore the reshaped segment in the eye. The eye heals by reformation of the outer cellular layer over the reshaped collagen layer. Alternatively, a layer of the cornea is opened up as a flap, an artificial or donor lenticular implant is inserted under the flap, and the flap is sutured up again.

It is a further object of this invention to provide an improved and less traumatic method and apparatus for reshaping the cornea of the eye.

Various other surgical techniques for reprofiling of the corneal surface have also been proposed. One increasingly common technique is radial keratotomy in which a set of radial incisions, i.e., resembling the spokes of a wheel, are made in the eye to remedy refractive errors, such as myopia (nearsightedness). As the incisions heal, the curvature of the eye is flattened, thereby increasing the ocular focal distance. The operation is not particularly suitable for correction of hyperopia (farsightedness) and can pose problems if the surgical incisions are uneven or too deep.

The use of a laser beam as a surgical tool for cutting incisions, a so-called laser scalpel, has been known for some time (see, for example, U.S. Pat. No. 3,769,963 issued to Goldman et al.). In 1980, a study was made of the damage which might be inflicted on the corneal epithelium by exposure to the recently developed excimer laser (see Taboada et al., "Response of the Corneal Epithelium to ArF excimer laser pulses," *Health Physics* 1981, Volume 40, pp. 677-683). At that period, surgical operations on the cornea were commonly carried out using diamond or steel knives or razor, and further, such techniques were still being studied (see, for example, Binder et al., "Refractive Keratoplasty," *Arch. Ophthalmol.*, May 1982, Vol. 100, p. 802). The use of a physical cutting tool in corneal operations, and the insertion of an implant under a flap, continue to be widely practiced up to the present day (see, for example, "Refractive Keratoplasty improves with Polysulfone Pocket Incision," *Ophthalmology Times*, Jul. 1, 1986).

It has been suggested in U.S. Pat. No. 4,665,913 issued to L'Esperance that controlled, ablative, photodecomposition of one or more selected regions of a cornea can be performed using a scanning action on the cornea with a beam from an excimer laser. Because of the scanning action, it is necessary for L'Esperance to bring his laser beam to a small spot, typically a rounded-square dot of size 0.5 mm by 0.5 mm.

L'Esperance suggests that myopic and hyperopic conditions can be reduced by altering the curvature of the outer surface of the cornea by repeatedly scanning the cornea with an excimer laser beam having this standard, small spot size but varying the field which is scanned during successive scans so that some areas of the cornea are scanned more often than others. In this way, it is claimed, the surface can be eroded by different amounts, depending on the number of times the spot scans the surface. Additionally, he suggests that certain severe myopic and hyperopic conditions may be treated with a reduced removal of tissue by providing the outer surface of the cornea with a new shape having Fresnel-type steps between areas of the desired curvature.

In practice, complex apparatus is required to cause a pulsed laser beam to scan with the precision required if the eroded surface is to be smooth. Thus, if successive sweeps of a scan overlap, there will be excessive erosion in the overlap area, whereas, if they fail to meet, a ridge will be left between the sweeps. The pulsed nature of excimer laser radiation also tends to exacerbate this problem. Additionally, the scanning method is inherently time-consuming even with highly refined techniques and apparatus, since the laser beam is only eroding a very small part of the total area to be treated at any given moment. Furthermore, such a scanning system can cause rippling effects on relatively soft materials, such as corneal tissue.

It is, therefore, a further object of the present invention to provide a method and apparatus for eroding a surface using a laser which does not require scanning of the area of the surface to be eroded.

Another technique for corneal reshaping involves the use of a laser photoablation apparatus in which the size of the area on the surface, to which the pulses of laser energy are applied, is varied to control the reprofiling operation. In one preferred embodiment, a beam-shaping stop or window is moved axially along the beam to increase or decrease the region of cornea on which the laser radiation is incident. By progressively varying the size of the exposed region, a desired photoablation profile is established in the surface. For further details on this technique see also, Marshall et al., "Photo-ablative Reprofiling of the Cornea Using an Excimer Laser: Photorefractive Keratoctomy," Vol. 1, *Lasers in Ophthalmology*, pp. 21-48 (1986), and U.S. Pat. No. 4,941,093 issued to Marshall et al., both of which are herein incorporated by reference.

Although this technique for varying the size of the exposed region is a substantial improvement over physical shaping (i.e., scalpel) techniques and laser spot scanning protocols, a considerable number of optical elements and control systems still are required for precise operation, particularly on human corneal tissue. There exists a need for better and simpler procedures for shaping surfaces, particularly the surfaces of biological tissues, such as corneal tissue.

SUMMARY OF THE INVENTION

A laser system and masking apparatus are disclosed for reprofiling material surfaces. The system comprises a laser means and a masking means disposed between the laser means and the target surface. The laser means provides a beam of radiation to the masking means. The masking means provides a predefined profile of resistance to erosion by laser radiation, such that, upon irradiation of the masking means, a portion of the laser radiation is selectively absorbed and another portion is transmitted to the surface in accordance with the mask profile to selectively erode the surface.

The masking means can comprise a mask and a support structure, preferably affixed to the laser or otherwise optically aligned therewith, such that the laser beam selectively passes through the masking means and onto the target surface. The masking means can further comprise a holder, which is attached to the support structure and secures the mask in place. The masking means may be independently fixed between the laser and surface, or it may be directly attached to the surface.

The masks of the present invention provide a predefined profile of resistance to the laser radiation. Such profiles can be provided by varying the light-absorbing properties of the mask material. When the efficiency of light-absorbing molecules is varied within the mask, the desired profile of erosion of the target surface may be obtained. In addition, the mask may be aspheric or toroidal at least on one surface or, for special cases, the surface shape may be irregular.

Conveniently, the mask material includes a matrix, which is highly transmissive and relatively impervious to intensity-dependent damage from laser radiation, and light absorption elements disposed within the matrix so as to define a resistance profile. Various light-absorbing materials can be employed, including, for example, ultraviolet-reactive dyes and the like.

The invention may further comprise any combination of mirrors, lenses and prisms, located either upstream or downstream of the masking means, or both, for imaging, focusing and redirecting the laser beam. Such configurations allow for the use of an oversized or undersized mask for greater convenience. Depending upon the application, the configuration of the optical elements may include focusing lenses, divergent lenses and collimating lenses, in various combinations and in a variety of shapes well-known to those skilled in the art.

According to another aspect of the invention, there is provided a method of reprofiling a surface comprising (a) optically aligning a laser means with a target surface, the laser means being operable to deliver laser radiation to the surface; and (b) disposing a masking means between the laser means and the target surface, the masking means having a predefined profile of resistance to laser radiation, such that, upon irradiation, a portion of the radiation is selectively absorbed and another portion is transmitted to the target surface in accordance with the mask profile to selectively erode the target surface.

The methods of the present invention are well-suited for controlled reprofiling of the cornea, particularly a region known as Bowman's membrane, which lies immediately below the uniform, extremely thin, epithelial layer of the cornea. In a corneal reprofiling operation, the epithelial layer can be removed mechanically using a scapel-like instrument, or it can be removed by laser ablation via the initial pulses of the laser. The surface of Bowman's membrane (or, in some instances, the underlying stromal tissue of the cornea, as well) is then selectively ablated using a mask according to the present invention. Following the reshaping operation, the epithelium heals and eventually reforms.

In such surgical applications, the laser source can be preferably an excimer laser, such as a UV Argon Fluoride laser operating at about 193 nanometers, which does not penetrate through the cornea. A minimum laser irradiance level is essential for ablation, but it is preferred not greatly to exceed this minimum threshold.

The present methods are not limited to corneal surgery of Bowman's membrane but rather also includes stromal eye surgery, generally, as well as other shaping operations of biological and non-biological material.

In addition, other gas mixtures resulting in different wavelengths, useful for different purposes, can be used such as Argon-Helium, Xenon-Flouride, Xenon-Chloride, Xenon-Bromide, Krypton-Flouride and Krypton-Chloride. Furthermore, chemical laser halogen and rare gas ion lasers, nitrogen lasers and carbon dioxide lasers can all be utilized.

The pulse repetition rate for the laser may be chosen to meet the needs of each particular application. Normally, the rate will be between about 1 and about 500 pulses/sec., preferably between about 1 and about 100 pulses/sec.

Suitable irradiation intensities vary depending on the wavelength of the laser and the nature of the irradiated object. For a given wavelength of laser energy applied to any given material, there will typically be a threshold value of the energy density below which significant erosion does not occur. Above the threshold density, there will be a range of energy density above which increasing energy densities give increasing depths of erosion, until a saturation level is reached. For increases in energy density above the saturation value, no significant increase in erosion occurs.

The threshold value and the saturation value will vary between wavelengths of laser energy and between target surface materials. However, for any particular laser wavelength and any particular material, the values can be found readily by experiment. For example, in ablation of the Bowman's membrane of the cornea alone or the membrane and the underlying corneal stroma by energy of wavelength 193 nm (the wavelength obtained from an ArF excimer laser), the threshold value is about 50 mJ per $cm^2$ per pulse, and the saturation value is about 250 mJ per $cm^2$ per pulse. There appears to be little benefit in exceeding the saturation value by more than a small factor, and suitable energy densities at the corneal surface are 50 mJ per $cm^2$ to one J per $cm^2$ per pulse for a wavelength of 193 nm.

The threshold value can vary very rapidly with wavelength. At 157 nm, which is the wavelength obtained from a $F_2$ laser, the threshold is about 5 mJ per $cm^2$ per pulse. At this wavelength, suitable energy densities at the corneal surface are 5 mJ per $cm^2$ to one J per $cm^2$ per pulse.

Most preferably, the laser system is used to provide an energy density at the surface to be eroded of slightly less than the saturation value. Thus, when eroding the cornea with a wavelength of 193 nm (under which conditions the saturation value is 250 mJ per cm² per pulse), it is preferable to provide to the photodecomposable mask and cornea pulses of an energy density of 100 to 200 mJ per cm² per pulse. Typically, a single pulse will erode a depth in the range 0.1 to 1 micrometer of collagen from the cornea.

The invention will next be described in connection with certain illustrated embodiments; however, it should be clear that those skilled in the art can make various modifications, additions and subtractions without departing from the spirit or scope of the invention. For example, the invention can be used in connection with corneal transplants or synthetic inlays where a donor insert is stitched into the patient's eye. Quite often, accidental over-tightening of the stitches introduces refractive errors in the cornea following the operation. At present, the transplant operation must be repeated or relaxing incisions must be made in the cornea. The present invention can provide an improved and less traumatic method for remedying such refractive errors.

Additionally, the present invention can be used to treat astigmatisms, corneal ulcers and keratomic growths which affect vision. In such instance, specific masks can be designed and constructed to selectively remove the corneal tissue which interfere with normal refraction.

Moreover, the teaching of the present invention can be applied to other biological tissues including lenticular implants, ligaments, cartilage, and bone, as well as non-biological material, requiring reprofiling.

BRIEF DESCRIPTION OF THE DRAWINGS

The invention will now be described by way of example with reference to the accompanying drawings, in which:

FIG. 4 A-C illustrates diagramatically the method of the present invention in reducing the curvature of an object; and FIG. 5A is a schematic illustration of a technique for manufacturing the mask of the present invention;

FIG. 5B is a overview of the mask illustrating the non-uniform distribution of light absorbing matter;

DETAILED DESCRIPTION

Figure 1:
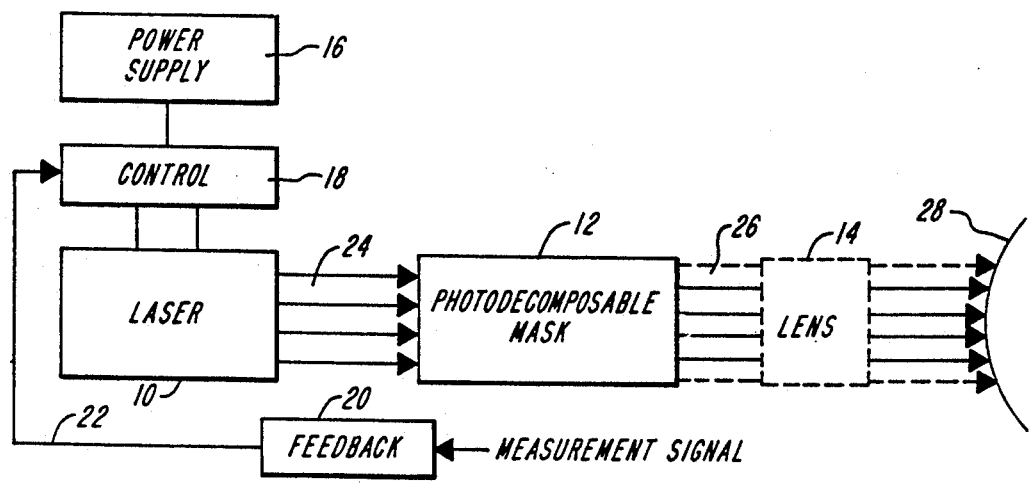
FIG. 1 is a schematic illustration of an apparatus for practicing a method of reprofiling the surface of an object, in accordance with the invention.

In FIG. 1, a laser 10 provides a radiation output 24 to a masking means 12 which provides a predefined resistance to the radiation whereby the mask's light absorbing properties are progressively destroyed. A portion of the laser radiation 26 is selectively transmitted in accordance with the composition of the mask and irradiates the surface 28 of the object which is to be reprofiled and which, as shown, may comprise the cornea of an eye. The system can further include one or more imaging lens elements 14 to image the mask onto the surface.

The laser is powered by a power supply unit 16 and control circuit 18 which can be adjustable to cause the laser to produce pulses of light at a specific frequency and intensity. To further control the laser, a feedback 20 can be provided which receives information from optical or other inspection of the masking means 12 and/or surface 28 while it is exposed to irradiation by the laser 10. A feedback path 22 communicates with the control circuit 18 for controlling the laser 10.

Figure 2:
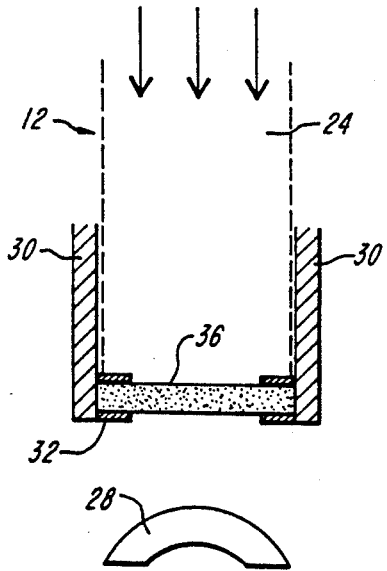
FIG. 2 is a more detailed illustration of a photodecomposable mask suitable for use in the apparatus of FIG. 1.

In FIG. 2, one embodiment of the masking means 12 of FIG. 1 is shown in more detail. As illustrated, the masking means 12 includes a support structure 30, which includes a holder 32 to secure the mask 36, which may be rigidly connected to the laser device or otherwise optically aligned such that radiation 24 from the laser can be selectively transmitted through the mask to produce the desired erosion of the surface by pulses of laser energy.

Various lens system can be used to focus or spread out the radiation that passes through the mask. For example, a zoom lens system can be disposed either upstream or downstream of the mask. Alternatively, the mask can be disposed between two cooperating lens elements. A converging lens arrangement enables the use of an oversized mask relative to the desired erosion of the target. For corneal applications, the light beam is preferably a collimated beam when it strikes the surface of the eye.

The selected mask material is photodecomposed by the laser radiation of light absorbing elements disposed within the mask. For example, the masks of the present invention can be formed from a matrix material which is transparent and impervious to erosion by laser radiation. Such matrix materials can include, for example, quartz, fused silica, magnesium fluoride, lithium fluoride, calcium fluoride, sapphire and other glassy materials, as well as high strength polymeric materials, such as polycarbonate, in some instances.

Preferably, light-absorbing dispersoids are disposed within the matrix to provide the resistance profile, such that UV light from the laser source is selectively absorbed by the dispersed elements. The mask is thus "bleached" by the laser radiation. The term "bleached" is used herein to encompass various photodecomposition reactions in which the light absorbing properties of the mask can be altered.

These changes can be permanent or temporary. If temporary, the bleached elements can be restored over time or by second optical exposure or by exposure to an electrical field. After bleaching, the mask becomes essentially transparent to further laser radiation. By control of the placement and density of such light absorbing materials, the desired resistance profile is obtained.

The light absorbing elements can be, for example, aromatic dye compounds and the like, such as (2,2 dichlorocyclopropyl) benzene, acetophenone, methylbenzoate, 1,4 napthoquinone, anthraquinone, ferrocene, ferrocene carboxylic acid, 1,1' ferrocene dicarboxylic acid, ferrocene carboxaldehyde, catechol, resorcinol, hydraquinone, 1,2,4 benzenetriol, 2-methylresorcinol, 3-methylcatechol, methylhydroquinone, 4-methylcatechol, phenyl boric acid, p-bromo-phenylboric acid, (1-methyl-butyl)benzene, and cyclopropylbenzene. For further details on light absorbing materials suitable for construction of masks, see Muller et al., "Studies of Organic Molecules as Saturable Absorbers at 193 nm," Vol QE-18 No. 11, *IEEE Journal of Quantum Electronics*, pp. 1865–1870 (1982).

Figure 3:
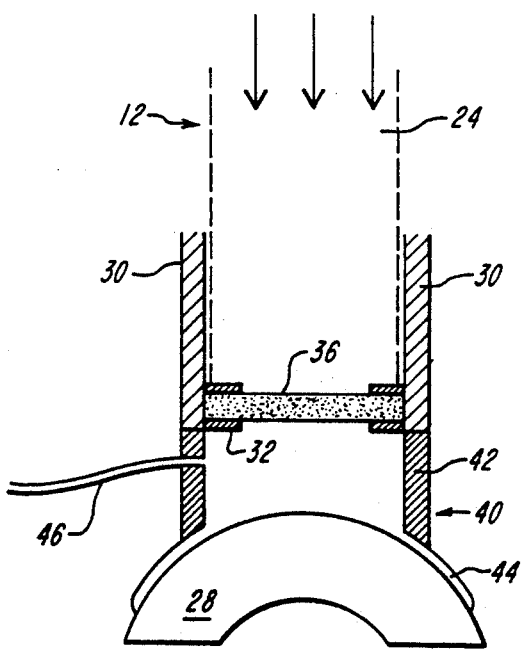
FIG. 3 is a detailed illustration of an alternative photodecomposable mask suitable for use in the apparatus of FIG. 1.

In FIG. 3, an alternative embodiment of the masking means of FIG. 1 is shown. As illustrated, the masking means 12 includes a support structure 30, which is attached to an eyepiece 40. The eyepiece 40 is hollow, has rigid vertical walls 42 and a flexible tube 46. Preferably the base 44 of the eyepiece 40 is shaped to be complimentary to the curvature of the surface of cornea 28, again, similar to FIG. 2, the masking means 12 includes a holder 32 and the mask 36. The masking means 12 with attachment eyepiece 40 can be placed upon the sclera of the cornea and secured using a vacuum suction drawn through flexible tube 46 leaving the surface of the cornea 28 unobstructed. The vacuum is sufficient to secure eyepiece 40 to the cornea 28. Alternatively, the eyepiece 40 can be manually secured to the eye or held in place by pressure or by a suitable adhesive, or combination of these means.

FIGS. 4A-4C illustrates the principle involved in eroding a surface to effect reprofiling thereof in accordance with the present invention.

In FIG. 4A-4C, the reference 28 denotes the object, such as the cornea of an eye, to be reprofiled. A uniform beam of radiation 24, obtained preferably from a pulsed UV laser source, irradiates mask 36 (a configuration of collimating lenses, well-known to those in the art, may be used upstream of the mask 36 to provide a uniform plane wave of radiation 24).

The non-uniformly dispersed light absorbing properties of the mask 36 are gradually and uniformly bleached, and an increasing area of radiation passes through and irradiates and erodes object 28.

According to the embodiment of mask 36 in FIG. 4A, radiation 24 is totally absorbed upon initial exposure. Over time, as depicted in FIG. 4B radiation 24 first wholly bleaches the light absorbing properties of the mask at location $t_2$ the least radiation resistant part of the mask, and irradiates location d of object 28. Radiation 24 continues to photodecompose or bleach the mask 36, and wholly destroys the light absorbing properties of the mask in the area centered at location $t_2$, such that a column of radiation, increasing in diameter over time and centered along line 48, irradiates and erodes object 28 at region 50.

In FIG. 4C, the radiation source 24 stops irradiating mask 36 when the radius of the transparent region in the mask increases in size to radius $t_1$. At that moment in time, the resultant erosion 50 of object 28 is completed.

Various techniques can be employed to manufacture the masks used in the present invention. These techniques included casting, molding and shaping from glass or polymer blanks. The light absorbing elements can be introduced during a molten or semimolten state or by solid state diffusion. Alternatively the dye can be deposited as a thin layer on a substrate and then coated with a protective overglass or the like.

In one technique, as shown in FIGS. 5A & 5B, a solid or liquid mask blank 70 of the matrix material can be spun on a rotating shaft 72, and the light absorbing material 74 can be deposited by a dispenser 76, which is adapted for radial movement along rail 78 (e.g., by a rack 79 and pinion 77 drive mechanism or the like). By varying the radial speed of the dispenser or the rate of dispensor flow, a non-uniform dispersion, on the molecular level, of the light absorbing matter can be readily obtained, as shown in FIG. 5B.

In an alternative technique, the mask blank 70 of the matrix material can be fabricated with a uniform dispersion of light absorbing matter. The blank can be cast or moulded to give the desired mask profile or the mask, itself, can be subsequently machined to give the desired profile.

Figure 6:
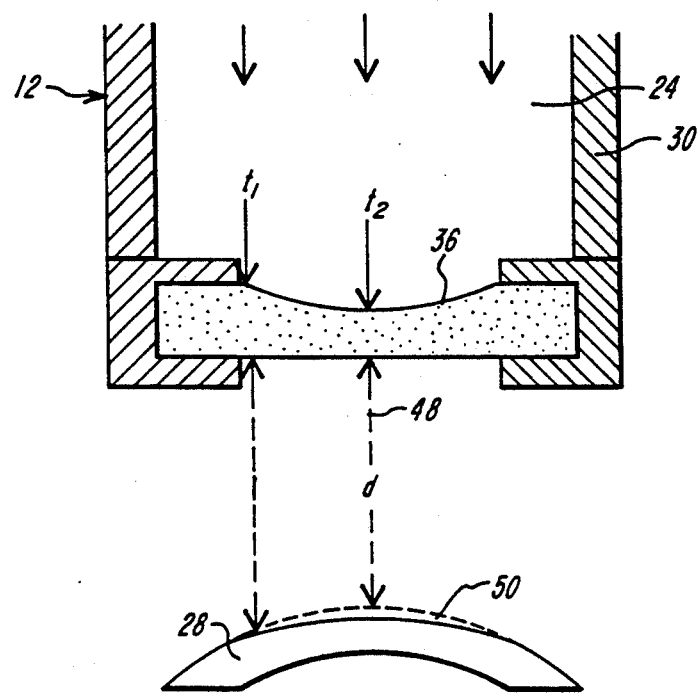
FIG. 6 is a detailed illustration of yet another alternative photodecomposable mask suitable for use in the apparatus of FIG. 1.

In an alternative embodiment of mask 36, as shown in FIG. 6, the same ablation results, as shown in FIG. 4C, can be obtained with a plano-concave mask having a uniform dispersion of light absorbing matter. The profile of mask 36 is not restricted to that of FIG. 6 but can be convexo-concave, plano-convex, convexo-convex or concavo-concave. In addition, the mask may be aspheric or torroidal, at least on one surface, or for special cases, the surface may be irregular.

Figure 7:
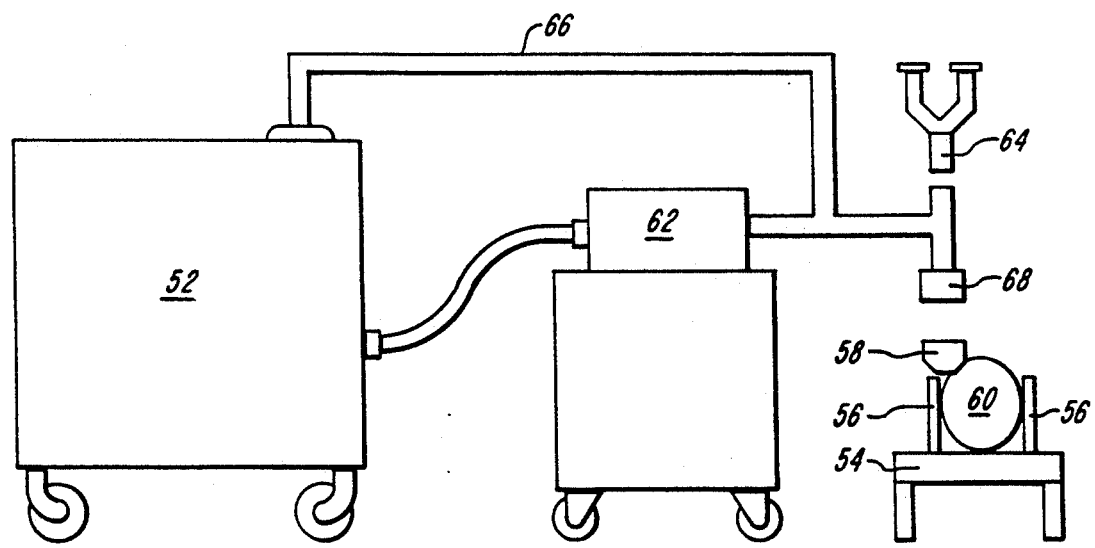
FIG. 7 shows a laser apparatus for measurement and reprofiling.

FIG. 7 illustrates an apparatus for performing a method of the present invention for reprofiling the cornea of a human eye. A laser and associated control circuitry is contained in a housing 52. The beam-forming optics, for providing a beam of desired shape and size, can also be contained within the housing 52, together with the laser power supply control circuits. An optical wave guide 66, which can be flexible or rigid, includes suitable mirrors, prisms and lenses, is provided to transmit the laser beam output from the housing 52 to the patient's head 60. The patient is lying face-upwards on an operating table 54. The operating table will support the patient's head against vertical movement. If desired, side supports 56 may also be provided to restrain sideways movement of the patient's head.

A photodecomposable mask, such as that shown in FIGS. 2-6, is disposed within masking apparatus 68 and is optically aligned with the patient's eye by markers disposed on immobilizing eyepiece 58 or by other techniques known in the art. The eye can be observed using surgical microscope 64 which is supported above the patient by any convenient means. The photodecomposable mask is manufactured, as described above, based on measurements of the patient's eye and has a profile which will impart the desired refraction correction upon erosion.

What is claimed is:

1. A masking apparatus for use in laser reprofiling of a target surface, the apparatus comprising: a support structure and a mask connected to the support structure, the mask comprising an optically transmission portion and a photobleachable composition having a distribution which provides a predefined profile of resistance to ablative laser radiation, whereby upon irradiation of the mask, the composition of the mask is progressively bleached, such that a portion of the laser radiation is selectively absorbed and another portion is transmitted to the target surface, in accordance with the mask profile to selectively ablate the target surface.

2. The apparatus of claim 1 wherein the mask varies in composition to provide the profile of resistance.

3. The apparatus of claim 1 wherein the mask varies in shape.

4. The apparatus of claim 1 wherein the mask further comprises a transmissive matrix and light absorbing matter distributed within the matrix.

5. The apparatus of claim 1 wherein the support structure further includes a holder adapted to receive the mask to which the mask is affixed.

6. The apparatus of claim 1 wherein the apparatus further includes at least one imaging lens for projecting radiation transmitted through the mask to the target surface.

7. A method of reprofiling a surface comprising:

locating a laser means in optical alignment with a target surface, the laser means being operable to deliver laser radiation to the target surface;

disposing a masking means between the laser means and the target surface, the masking means comprising an optically transmissive portion and a photobleachable composition having distribution which provides a predefined profile of resistance to laser radiation; and irradiating the masking means with laster radiation of sufficient intensity to ablate the target surface, whereby the light-absorbing properties of the mask are progressively bleached, such that a portion of the radiation is selectively absorbed and another portion is transmitted to the target surface, in accordance with the mask profile to selectively ablate the target surface.

8. The method of claim 7 wherein the the step of providing a masking means further comprises providing a masking means in which the photobleachable composition varies in distribution to provide the profile of resistance.

9. The method of claim 7 wherein the method further comprises locating the laser means and the masking means in optical alignment with corneal tissue, and then irradiating the masking means to selectively erode the corneal tissue.

10. The method of claim 7 wherein step of providing masking means further comprises providing a masking means which varies in shape to provide the profile of resistance.

11. The method of claim 10 wherein the step of providing a masking means further comprises providing masking means which varies in thickness to provide the profile of resistance.

* * * * *